US010214470B2

(12) United States Patent
Dubois et al.

(10) Patent No.: US 10,214,470 B2
(45) Date of Patent: Feb. 26, 2019

(54) SYNTHESIS OF GUERBET ALCOHOLS (71) Applicants: Arkema France, Colombes (FR); Warter Fuels Spólka Akcyjna, Warsaw (PL)

(72) Inventors: Jean-Luc Dubois, Millery (FR); Wei Zhao, Breda (NL); Raf Edward Anna Roelant, Breda (NL); Hans Keuken, Wuustwezel (BE); Pedro Miguel Ramos Borges, Clermont-Ferrand (FR)

(73) Assignees: Arkema France, Colombes (FR); Warter Fuels Spolka Akcyjna, Warsaw (PL)

( * ) Notice: Subject to any disclaimer, the term of this patent is extended or adjusted under 35 U.S.C. 154(b) by 160 days.

(21) Appl. No.: 14/627,727

(22) Filed: Feb. 20, 2015

(65) Prior Publication Data
US 2015/0246863 A1   Sep. 3, 2015

(30) Foreign Application Priority Data

Feb. 28, 2014   (EP) .................................... 14157386

(51) Int. Cl.
*C10L 1/02* (2006.01)
*C07C 29/34* (2006.01)
(Continued)

(52) U.S. Cl.
CPC .............. *C07C 29/34* (2013.01); *C07C 1/24* (2013.01); *C07C 2/06* (2013.01); *C10L 1/023* (2013.01);
(Continued)

(58) Field of Classification Search
CPC ......... C07C 29/34; C07C 31/125; C07C 1/24; C07C 2/06; B01J 2219/00006;
(Continued)

(56) References Cited

U.S. PATENT DOCUMENTS 2,828,326 A   3/1958 Doerr et al.
3,514,493 A   5/1970 Pregaglia et al.
(Continued)

FOREIGN PATENT DOCUMENTS

EP       2080749 A1     7/2009
WO    WO91/04242 A  *  4/1991
(Continued)

OTHER PUBLICATIONS

Extended European Search Report for Application No. EP 14157386.5 published by the EPO, dated Jul. 31, 2014, including corresponding Communication, and 1-page Annex (EPO Form P0459).
Olson, et al., "Higher-Alcohols Biorefinery Improvement of Catalyst for Ethanol Conversion," Applied Biochemistry and Biotechnology, 2004, 913-932, vol. 113-116, Humana Press Inc.
(Continued)

*Primary Examiner* — Latosha Hines
(74) *Attorney, Agent, or Firm* — Kilyk & Bowersox, P.L.L.C.

(57) ABSTRACT

A method and system for preparing a mixture of Guerbet alcohols where one or more primary alcohols of the formula $RCH_2CH_2OH$ are provided, with R representing hydrogen or a straight or branched chain alkyl group of 1 to 14 carbon atoms. A base and a catalyst are provided, which are mixed with the primary alcohol(s). The resulting mixture is heated to a process temperature above the boiling point of water under reaction conditions and the water resulting from the thus obtained condensation and dehydration of the primary alcohols is then removed constantly. When the Guerbet reaction has reached a certain stage, at least part of the reaction mixture is removed, followed by a separation of the desired Guerbet alcohols from the removed part of the reaction mixture. The other alcohols are then returned to the reaction mixture for obtaining a higher amount of the desired Guerbet alcohols.

13 Claims, 2 Drawing Sheets (51) Int. Cl.
*C10L 1/182* (2006.01)
*C07C 1/24* (2006.01)
*C07C 2/06* (2006.01)

(52) U.S. Cl.
CPC .............. *C10L 1/026* (2013.01); *C10L 1/1824* (2013.01); *B01J 2219/00006* (2013.01); *C10L 2230/20* (2013.01); *C10L 2270/023* (2013.01); *C10L 2270/026* (2013.01); *C10L 2270/04* (2013.01)

(58) Field of Classification Search
CPC ........ C10L 1/023; C10L 1/026; C10L 1/1824; C10L 2230/20; C10L 2270/023; C10L 2270/026
See application file for complete search history.

(56) References Cited

U.S. PATENT DOCUMENTS 8,318,989 B2* 11/2012 Kourtakis ............... C07C 29/34
568/902.2
2003/0181770 A1* 9/2003 Both ....................... C07C 29/34
568/905

FOREIGN PATENT DOCUMENTS

WO     WO 9104242 A1 * 4/1991 ............. C07C 29/34
WO     WO91004242 A1 * 4/1991

* cited by examiner

SYNTHESIS OF GUERBET ALCOHOLS

FUNDING

The research leading to these results has received funding from the European Union Seventh Framework Programme (FP7/2007-2013) under grant agreement No 241718 Euro-BioRef.

CROSS-REFERENCE TO PRIORITY APPLICATION

The present application claims the priority benefit of European Patent Application No. 14157386.5, filed Feb. 28, 2014, which is incorporated in its entirety herein.

FIELD OF THE INVENTION

The present invention relates to the synthesis of long chain Guerbet alcohols, and in particular to the synthesis of mixtures of Guerbet alcohols containing long-chain multi-branched Guerbet alcohols.

BACKGROUND OF THE INVENTION

The term "Guerbet alcohols" is commonly used to describe alcohols formed by Guerbet reaction, named after Marcel Guerbet, which is an auto condensation converting a primary aliphatic alcohol into its β-alkylated dimer alcohol with loss of one equivalent of water. The Guerbet reaction requires a catalyst and elevated temperatures.

Guerbet alcohols are saturated primary alcohols with a defined branching of the carbon chain. They are well known in the state of the art.

The term Guerbet alcohol as used in this specification is to be understood as a monofunctional, primary alcohol comprising at least one branching at the carbon atom adjacent to the carbon atom carrying the hydroxyl group. Chemically, Guerbet alcohols are described as 2-alkyl-1-alkanols, but in the present specification Guerbet alcohols comprise also multi-branched alcohols (multiple alkyl alcohols).

The reaction mechanism leading to Guerbet alcohols comprises essentially the following steps: First, a primary alcohol of the formula $RCH_2CH_2OH$, wherein R may be hydrogen or a straight or branched chain alkyl group, is dehydrogenated (or oxidised) to the respective aldehyde. In the following, two aldehyde molecules undergo an aldol condensation to an α,β-unsaturated aldehyde, which is finally hydrogenated to the "dimer" alcohol. The catalyst used for this reaction may be of alkaline nature (e.g. potassium hydroxide, sodium hydroxide, sodium tert-butoxide, etc.) possibly in the presence of a platinum or palladium catalyst. Usually the reaction takes place under heating and possibly pressurization. An overview of a Guerbet condensation process is given in the illustration below:

A Guerbet alcohol may also have two or more branches, particularly if it is the product of two or more subsequent condensation reactions. For example, 2-ethyl-1-hexanol, the Guerbet dimer of 1-butanol, may react with 1-propanol to yield 4-ethyl-2-methyl-1-octanol. This further increases the variety of Guerbet alcohols.

An example of a process for preparing branched dimer alcohols based on the Guerbet reaction is for instance disclosed in the patent specification EP 0 299 720 B1 assigned to Exxon Chemical Patents Inc. The process comprises steps of first combining the primary alcohol mixture with KOH and NaOH and heating the mixture until the base dissolves. Thereafter a platinum catalyst on activated carbon support is added and heated to reflux with water being evolved and removed as it is formed.

Another example of a process for dimerizing alcohols in a manner of Guerbet reaction is disclosed in patent application US 2012/0220806 A1 filed by Cognis IP management GmbH. The process converts one or more starting alcohols having 2 to 72 carbon atoms and one to three OH-groups per molecule in the presence of a base (KOH), a carbonyl compound and a metallic hydrogenation catalyst. The process is limited to the use of alcohols that have at least one primary or secondary OH-group and a carbon atom bearing at least one hydrogen atom as a substituent that is directly adjacent to the carbon atom having the primary or secondary OH-group.

For a large scale production of multi-branched Guerbet alcohols, however, an improved manufacturing process is required that further allows to control the final distribution of Guerbet alcohols with respect to carbon number and branching type and number.

SUMMARY OF THE INVENTION

A respective process is provided by a method for preparing a mixture of Guerbet alcohols comprising the following steps: providing a starting material comprising one or more primary alcohols of the formula $RCH_2CH_2OH$, where R is hydrogen or a straight or branched chain alkyl of 1 to 14 carbon atoms, preferably R is a straight or branched chain alkyl of 1 to 12 carbon atoms, more preferably of 2 to 10 carbon atoms, and in particular 3 to 8 carbon atoms; providing a base; providing a catalyst; mixing the starting material with the base and the catalyst and heating the thus obtained reaction mixture to a process temperature above the boiling point of water or its azeotropes with the components in the system under reaction conditions while removing the water resulting from the thus obtained condensation and dehydration of the primary alcohols; removing at least part of the reaction mixture; separating the desired Guerbet alcohols from the removed part of the reaction mixture; and returning the other alcohols and optionally other intermediates from the removed part of the reaction mixture to the reaction mixture.

A respective process is further provided by a system for synthesising Guerbet alcohols from a starting material comprising one or more primary alcohols of the formula $RCH_2CH_2OH$, where R is hydrogen or a straight or branched chain alkyl of 1 to 14 carbon atoms, preferably R is a straight or branched chain alkyl of 1 to 12 carbon atoms, more preferably of 2 to 10 carbon atoms, and in particular 3 to 8 carbon atoms, whereby the system comprises: a reactor adapted for receiving the starting material, a base, and a catalyst to form a reaction mixture, and for heating the reaction mixture to a temperature above the boiling point of water or its azeotropes with the components in the system under reaction conditions to obtain a Guerbet condensation and dehydration process; a water separation unit connected to the reactor and adapted to receive from the reactor vapour evolving in the progress of the Guerbet condensation and dehydration process, and to remove water from the vapour; an after-treatment system connected to the reactor and adapted to receive from the reactor at least part of the reaction mixture, separating the desired Guerbet alcohols from the removed part of the reaction mixture, and returning the other alcohols and optionally other intermediates from the removed part of the reaction mixture to the reactor.

It should be noted in this context that the terms "comprise", "include", "having", and "with", as well as grammatical modifications thereof used in this specification or the claims, indicate the presence of technical features such as stated components, figures, integers, steps or the like, and do by no means preclude the presence or addition of one or more other features, particularly other components, integers, steps or groups thereof.

In advantageous embodiments of the method specified above, the starting material further contains secondary alcohols, ketones and aldehydes, and hydrogen is added to the reaction mixture or the removed part of the reaction mixture enabling a higher variety of Guerbet alcohols. As will be appreciated by those skilled in the art, the starting material may also contain unavoidable impurities in minor amounts.

In advantageous embodiments of the method specified above, the starting material contains at least two primary alcohols selected from the group comprising n-propanol, n-butanol, n-pentanol, n-hexanol enabling a mixture of higher carbon number multi-branched Guerbet alcohols.

In further advantageous embodiments of the method specified above, the base is at least one of sodium tert-butoxide, potassium hydroxide, and sodium hydroxide, the first base being a strong base enabling a high alcohol conversion process of the Guerbet condensation reaction even at atmospheric pressure, the other bases allowing a very cost effective formation of Guerbet alcohols at higher process pressures and temperatures.

According to further advantageous embodiments of the method specified above, heterogeneous bases, which may optionally be doped with metals like for example Ni, Pd, or Cu are used. Examples for heterogeneous bases are hydrotalcites, hydroxyapatite, alkali and alkaline earth doped mixed oxides, or oxinitrides such as vanadium-aluminium-phosphorous-oxinitride VAlPON, aluminium-phosphorous-oxinitride AlPON.

In also advantageous embodiments of the method specified above, the catalyst is selected from the group consisting of Cu—Zn-oxide, Cu-chromite, Raney Ni, Ni—MgO/$SiO_2$, Pd/C, Pt/C, metal, as for example Ni, Pd, Cu, doped heterogeneous bases and $Pd(OAc)_2$, whereby $Pd(OAc)_2$ is particularly preferred for lower process pressures like atmospheric pressures. The other, heterogeneous catalysts enable a wider distribution of the Guerbet alcohols achieved.

In also advantageous embodiments of the method specified above, a particularly advantageous configuration comprises a fixed bed, or a slurry fluidised bed or a mobile bed of a solid heterogeneous catalyst.

Embodiments of the method specified above may further be implemented with the alcohols returned to the reaction mixture having a lower boiling point than the desired Guerbet alcohols allowing the lighter than desired alcohols to be returned to the reaction process.

In particular embodiments of the method specified above, the process temperature is equal to or higher than the boiling point of water or its azeotropes with the components in the system under process conditions, and does not exceed the boiling point of the starting material for maximising the conversion rate of the Guerbet condensation process. Since the boiling point of the starting material increases with the pressure, higher process pressures allow higher process temperatures. The reaction temperature is determined by the lowest boiling point compound when operating at reflux conditions. The reaction process is effectively performed in liquid phase at a pressure of 1 bar or higher. The term "in liquid phase" is hereby to be understood as "in a gas-liquid condition" since part of the reactants and the water produced should be in gas phase.

In preferred embodiments of the method described above, and in particular when using bio-alcohols for the Guerbet synthesis, the starting material is pre-treated with respect to removing acidic components and/or water prior to being fed to mixing for preventing a degradation of the base and an inhibition of the condensation process.

In preferred embodiments of the system specified above, the after-treatment system comprises a first after-treatment system adapted to separate a catalytic component and an alkaline component as well as degradation products of the former, such as salts resulting from neutralization of the alkaline from the part of the reaction mixture received from the reactor, and a second after-treatment system connected to the first after-treatment system and adapted to separate the desired Guerbet alcohols from the part of the reaction mixture treated by the first after-treatment system and to return the other alcohols from that mixture to the reactor. A respectively configured after-treatment system enables a catalyst recovery and a purification of the alcohol components of the mixture received from the reactor.

In order to obtain alcohol components substantially free of water, the second after-treatment system comprises in further preferred embodiments a liquid-liquid mixer-settler configuration adapted to receive the reaction mixture treated by the first after-treatment system and to provide a phase separation of the components present in the mixture, an alcohols column adapted to receive the primarily alcohol components containing phase from the liquid-liquid mixer-settler configuration and to dry the alcohol components, and an alcohols splitter column connected to the alcohols column and the reactor, and being adapted to separate the desired Guerbet alcohols from the dried alcohol components and to return the remaining dried alcohols to the reactor.

For achieving a low contaminant wastewater, favoured embodiments of the system specified above have the second after-treatment system further comprising a water column adapted to receive the primarily water containing phase from the liquid-liquid mixer-settler configuration, separate water from that phase, and return alcohols containing water to the liquid-liquid mixer-settler configuration.

For returning the alcoholic components of the vapour received from the reactor back into the reactor and for purifying the azeotropic composition formed by the water separation, the water separation unit is in particularly effective embodiments of the system specified above further adapted to return the vapour components different to the separated water to the reactor, and to provide the still alcohols containing separated water to the liquid-liquid mixer-settler configuration.

In the product return loops described above, one or several systems can be provided to remove certain components which have the tendency to show ever increasing concentrations in this loop because they have no outlet and because they are not converted in the reactor, which have undesirable effects in the reactor or elsewhere in the loop, or which, through reaction, give rise to the formation of components having such undesirable effects. Such removal systems can be selective, e.g. distillation columns, or non-selective, i.e., simple purge streams.

Particularly when reacting bio-alcohols, particularly preferred embodiments of the system specified above further comprise a pre-treatment facility adapted to remove acidic and ester components and/or water from the starting material prior to supplying the starting material to the reactor in order to prevent a degradation of the base forming part of the catalytic system and an inhibition of the condensation process.

Guerbet alcohols obtained by a method as specified above and/or by using a system as specified above are particularly useful as additives for fuels like diesel or jet fuels, where they increase the electric conductivity and thus decrease the probability of ignition by static electricity, as precursors for esters such as acrylates, methacrylates, phthalates or the like, as to be hydrodeoxygenated precursors of gasoline or aviation fuel constituents, such as aviation gasoline and jet fuel, or as precursors of surfactants that are e.g. suited for utilisation in petroleum industry operations or as precursors of alpha-olefins and their polymers and oligomers.

Further features of the invention will be apparent from the following description of exemplary embodiments of the invention together with the claims and the attached figures. It is noted that the present invention is only limited by the scope of the appended claims, and not to the particular examples of embodiments described. Embodiments of the invention may thus combine features described in the context of different exemplary embodiments and may also combine only part of the features described for a particular embodiment or a combination of particular embodiments. Embodiments of the present invention may further also have additional features not described in the context of the exemplary embodiments given herein.

BRIEF DESCRIPTION OF THE DRAWINGS

A better understanding of the features and advantages of the present teachings can be achieved by reference to the accompanying drawings, which are intended to illustrate, not limit, the present teachings.

DETAILED DESCRIPTION OF THE INVENTION

Figure 1:
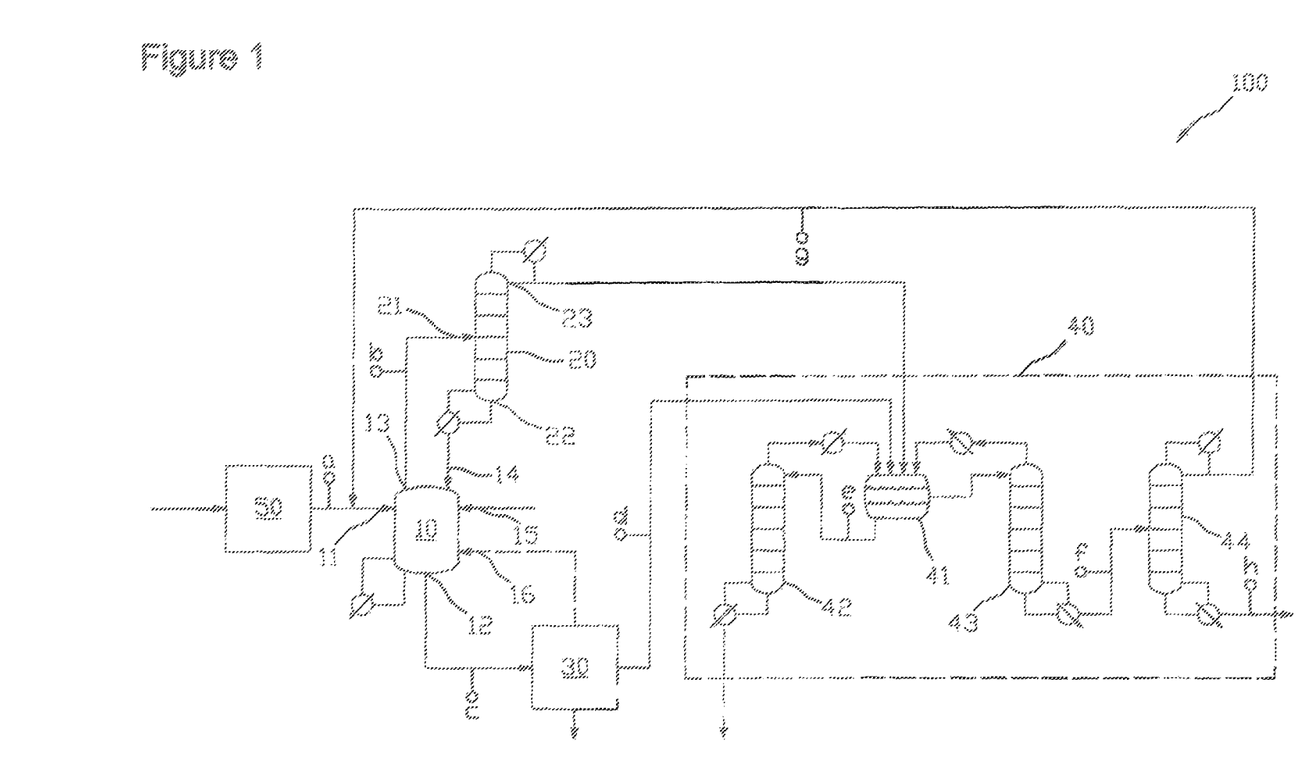
FIG. 1 shows a simplified piping and instrumentation diagram of a process engineering system for a synthesis of Guerbet alcohols from a starting material comprising one or more primary alcohols.

FIG. 1 shows a simplified piping and instrumentation diagram of a process engineering system 100 for a synthesis of Guerbet alcohols from one or more primary alcohols.

The synthesis itself takes place in reactor 10 comprising a feed port 11 for introducing feedstock into the reactor 10, and a discharge port 12 for discharging material from the reactor 10. The reactor 10 is further provided with a vapour outlet port 13 and a reflux inlet port 14, both connected to a water separation unit 20. In preferred embodiments, the reactor further comprises a base inlet port 15 and catalyst inlet port 16 for enabling a separate feeding of a base and/or a catalyst into the reactor. The reactor may have further ports (not shown in the Figure) that may be used for other purposes like process control and addition of further reactants, e.g. hydrogen that may be added to the reactor at a later stage of the reaction for facilitating the hydrogenation step in the reaction sequence of Guerbet alcohol formation, or hydrogen capture agents, such as olefins, that may be added at an earlier stage of the reaction to facilitate the formation of the intermediate aldehydes.

The reactor can be a stirred tank reactor, a fixed bed reactor, a mobile bed reactor, a fluidized bed reactor with a homogeneous or heterogeneous catalyst, where the base can be either homogeneous or heterogeneous, and in the latter case can eventually be used as catalyst or as the support phase of an active catalyst.

As explained above, the Guerbet reaction requires a multi-functional catalytic system for enabling a dehydrogenation and a hydrogenation, which are both promoted by a metallic and/or basic function, an aldolisation and a dehydration, which are promoted by acidic-basic properties. Upon a start of operation, the reactor 10 is therefore filled up to a certain level with a starting material of primary alcohols, a base, and a catalyst, whereby the mixture is heated to a process temperature above the boiling point of water under reaction conditions. The synthesis process can be carried out at atmospheric pressure (1 bar) or higher pressures, like for instance up to 10 bar or even higher, for example 20 bar, whereby higher pressures usually allow higher process temperatures for example temperatures up to 200° C. and even higher, e.g. 250° C.

Since the water formed during the reaction may have a negative effect on the further progress of the reaction, it is continuously removed from the reactor. To this end, vapours including steam, i.e. water vapour, evolving during the reaction process are removed from the reactor through vapour outlet port 13 and fed into the water separation unit 20 via the unit's vapour inlet port 21. The water separation unit 20 removes the water contained in the vapour received from the reactor 10. The water separation unit 20 is further configured to recycle part of the alcohols present in the vapour received and to return these via the unit's alcohol outlet port 22 and the reactor's reflux inlet port 14 back into the reaction mixture located inside the reactor 10. The separated water, usually still containing some of the light alcohols or other products originating from the reaction mixture, is discharged from the water separation unit through the water outlet port 23. Examples for water separation units 20 are water separation columns, Dean-Stark traps, molecular sieves, membranes, or the like. Preferred are distillation separation columns, including rotating packed bed units (HiGee), heat integrated distillation units (HiDic) and any alternative technology suited for the separation of close boiling point compounds.

Between reactor 10 and water separation unit 20, or integrated in the water separation unit 20, a separator (not shown in the figure), e.g. flash, column or purge/splitter, can be optionally provided for removing some light components, to facilitate the operation of the water separation unit 20.

In some embodiments, a stirrer (not shown in the Figure) is disposed within reactor 10 for stirring the reaction mixture and facilitating a separation between the liquid and the vapour phases in the reactor. The heating of the reaction can be accomplished using internal coils, a heating jacket, an external heat-exchanger with external recirculation, or any other suitable means.

For separating the desired Guerbet alcohols, at least part of the reaction mixture is discharged from the reactor 10 via the discharge port 12. When applying a batchwise synthesis process, the reaction is performed until completed, which, since the production of water decreases towards the end of the process, can be determined by monitoring the water content of the vapour fed into the water separation unit 20. The end of the reaction is then determined when the production of water has sufficiently slowed down. Alternatively, the process will be ended when the desired reaction time has been reached, whereby the desired reaction time can be determined based on experiments and/or simulations. When applying a more continuous processing, part of the reaction mixture is removed from a certain stage of the reaction, and supplied to a separation system where the desired Guerbet alcohols are separated and the lighter alcohols returned to the reactor 10. Once started, the removal of part of the reaction mixture can be effected on a continuous or discontinuous basis. Returning the alcohols lighter than the desired long-chain Guerbet alcohols to the reactor 10 reintroduces these alcohols into the reaction process to thereby increase the process yield with respect to the amount of primary alcohols used.

Prior to a separation of the desired Guerbet alcohols from the other alcohols, the discharged reaction mixture is preferably processed in a first after-treatment system 30 adapted to remove the catalyst, the base and possibly degradation products of the former, such as salts formed by neutralization of the base. The separation of the catalyst from the discharged reaction mixture depends on the respective catalyst's properties. When using e.g. palladium(II)-acetate (Pd(OAc)$_2$) as is preferred in some embodiments, the catalyst may be washed out with water allowing it to precipitate. The catalyst can then be filtered out, optionally dried, and returned to reactor 10 using catalyst inlet port 16 or can be eliminated from the process loop and regenerated into fresh catalyst. The homogeneous base may be removed using an acid, which may for example include an ion exchange resin or electrodialysis, and separating the resulting salt from the mixture. The resin may be regenerated by an acid wash. The first after-treatment system 30 may further also be configured to remove other solids from the discharged reaction mixture.

Optionally an additional hydrogenation reactor (not shown in the figure) is provided downstream of the reactor 10, e.g. downstream of the first after-treatment system 30. The aim of this reactor is to complete the dehydration-hydrogenation of the reaction intermediates and to enrich the stream in Guerbet alcohols. Any conventional catalyst can be used for this step and preferably catalysts containing Ni, or a noble metal. A supplement of hydrogen ($H_2$) is also fed to this reactor.

When operating the system 100 in a continuous or stepwise continuous way, the amount of material discharged from the reactor is replaced in part by the lighter alcohols from the separation system 44 that are returned into the reactor, newly added feedstock, and the amounts of base and catalyst required for balancing the respective losses caused by the discharge of materials from the reactor 10. While the base replacement is advantageously effected using base inlet port 15, replenishment of the catalyst is preferably performed using catalyst inlet port 16.

For the separation of the desired Guerbet alcohols and the recovery of the alcohols to be returned to the reaction chamber 10, a second after-treatment system 40 is used which comprises a liquid-liquid mixer-settler (or decanter) configuration 41, a water column 42, an alcohols column 43, and an alcohols splitter column 44.

The liquid-liquid mixer-settler configuration 41 receives the output from the first after-treatment system 30 as well as the output from the water outlet port 23 of the water separation unit 20. The latter is necessary, because it is not always possible to obtain a pure aqueous stream at the water outlet port 23 due to the water forming azeotropes with the alcohols received from the reactor 10 and the water concentration being subazeotropic. The azeotropic composition from the water outlet port 23 of the water separation unit 20 and the output from the first after-treatment system 30 are initially introduced into the mixer where a phase separation is expected to occur.

The organic fraction from the settler is fed into to the alcohols column 43, e.g. a stripping column, where the dried alcohols are obtained at the bottom while an azeotropic alcohol/water mixture is taken from the top, condensed, cooled and finally returned to the mixer. The operation of the alcohols column 43 is preferably effected under vacuum conditions (e.g. at 0.4 bar abs.) enabling a lowering of the working temperature of the reboilers.

Optionally between the liquid-liquid mixer-settler 41 and the alcohols column 43, there is an additional separation unit (not shown in the figure), as e.g. flash, column or purge/splitter, to avoid building-up of some light components.

The aqueous fraction from the settler is fed into the water column 42, e.g. a stripping column, where it is split into a water bottom stream representing the systems waste water and an azeotropic mixture on the top that is returned to the mixer after having been condensed and cooled. Also the water column 42 is preferably operated under vacuum conditions (e.g. at 0.4 bar abs.).

The dried alcohols obtained at the bottom of the alcohols column 43 are separated by distillation in a single alcohols splitter column 44, based on their respective differences in volatility. The lighter alcohols are returned to the reactor while the heavier ones are obtained as product or are used for further processing like for instance hydrogenation and/or dehydration. The average size of the thus separated products can be controlled by setting the separation characteristics of the column 44.

In the return loops described above, one or several systems can be provided to remove certain components which have the tendency to show ever increasing concentrations in this loop because they have no outlet and because they are not converted in the reactor, which have undesirable effects in the reactor or elsewhere in the loop, or which, through reaction, give rise to the formation of components having such undesirable effects. Such removal systems can be selective, e.g. distillation columns, or non-selective, i.e., simple purge streams.

As feedstock starting materials composed of primary monofunctional alcohols are used. The starting materials can be of fossil origin or obtained from renewable resources. As materials from renewable resources, plant materials, materials of animal origin or materials resulting from recovered materials (recycled materials) may be used. Plant materials may be for example derived from sugar and/or starches containing plants, such as sugar cane, sugar beet, corn, wheat, potato, macro-algae and the like. The primary alcohols may be produced by fermentation from biomass using biocatalysts. The biocatalyst may be one or more microorganism (e.g. yeast, bacteria, fungi) capable of forming one or a mixture of two or more different alcohols. Fermentation methods and the respective microorganisms used for fermentation are known in the state of the art, and e.g. described in WO 2009/079213. Alcohols can also be mixed with ketones and aldehydes of biobased or fossil origin.

When primary alcohols derived from biomass instead of petro-chemical origins are used, the carbon content of the resulting Guerbet alcohols originates from atmospheric carbon dioxide captured through photosynthesis, thus reducing the carbon dioxide impact on the environment caused by a consumption of the Guerbet alcohols. Alcohols derived from biomass conversion are called bio-alcohols. Bio-alcohols are thus identifiable by their $^{14}C$ content. Carbon taken from living organisms and in particular from plant matter used to manufacture bio-alcohols is a mixture of three isotopes, $^{12}C$, $^{13}C$, and $^{14}C$, with the ratio of $^{14}C$ to $^{12}C$ being kept constant at $1.2 \cdot 10^{-12}$ by the continuous exchange of the carbon with the environment. $^{14}C$ is radioactively unstable with its concentration therefore decreasing over time. With a half-life of 5,730 years, the $^{14}C$ content is, however, considered to be constant from the extraction of the plant matter up to the manufacture of bio-alcohols thereof and even up to the end of the bio alcohol's final use. An alcohol can be identified as bio-alcohol when the $^{14}C/^{12}C$ ratio is strictly greater than zero and smaller than or equal to $1.2 \cdot 10^{-12}$.

The feedstock may contain acidic components, as it is for example known from bio-alcohols, compromising the performance of the Guerbet process through neutralisation of some of the alkaline components present in the reactor 10. The feedstock may further contain ester components, which are preferably removed prior to being supplied to the reactor. Preferred embodiments of the system 100 therefore provide for a preparatory treatment of the feedstock prior to supplying the feedstock to reactor 10. The preparatory treatment of the feedstock is performed in the pre-treatment facility 50 either by a process eliminating the presence of acids or esters by capture, e.g. ion exchange, or neutralisation, e.g. with an appropriate alkaline agent. Since water may be introduced into the feedstock through contact with an aqueous solution during an alkaline pre-treatment or may already have been part of the original feedstock, and since water is known to affect the Guerbet process, preferred embodiments of the pre-treatment facility 50 are further configured to remove water from the feedstock before it is fed into the reactor 10. When only water needs to be removed from the reactant, this step can be combined with the dehydration of reaction products and fresh reactants can be fed to the unit 43 or 42 or 41 depending on their water content. When acids need to be removed from the reactant, this step can be combined with the hydrogenation—finishing step included between unit 30 and 41, not shown on the figure.

The Guerbet reaction enables a preparation of higher alcohols from light alcohols and in particular from bio-alcohols. The Guerbet reaction requires, however, a catalytic system providing a dehydrogenation, aldolisation, dehydration, and hydrogenation. The catalytic system is typically composed of a catalyst and a base.

As catalysts homogeneous and heterogeneous metallic catalysts may be used. Homogenous catalysts have one catalytically active component while heterogeneous catalysts have more than one catalytically active component. An example for a homogeneous catalyst is $Pd(Ac)_2$. Examples for heterogeneous metallic catalysts are Pd(2%)/C, Pt/C, Cu—Zn—O, Cu—Cr—O, alkali or alkaline earth doped oxides, hydrotalcites and hydroxylapatites doped with metals as for example Ni, Pd, Cu, Raney Ni, Ni—MgO/SiO$_2$. Although the effect of the catalyst on the Guerbet reaction cannot be assessed isolated from the alkaline component of the catalytic system, a tendency has been observed that heterogeneous catalysts promote a formation of a greater variety of reaction products, while homogeneous catalysts boost a formation of particular reaction products. Heterogeneous catalysts and particularly Ni/MgO/SiO$_2$ are preferred for the production of higher molecular weight Guerbet alcohols. Furthermore, heterogeneous catalysts like Ni/MgO/SiO$_2$ facilitate the product separation.

It has been found that a strong base is beneficial for the Guerbet process, particularly when performed with relative low temperatures at atmospheric pressure. In preferred embodiments of synthesising Guerbet alcohols from primary alcohols with a system 100 as described above, sodium tert-butoxide (t-BuONa) is used as alkaline component of the catalytic system. The reaction process can be carried out at atmospheric pressure with a process temperature of above 104° C., whereby temperatures corresponding to the boiling temperature of the alcohol mixture fed into the reactor 10 are preferred. Using for example a feedstock containing 2.9 wt % 1-propanol, 57.8 wt % 1-butanol, 23.7 wt % 1-pentanol, and 15.3 wt % 1 hexanol, the process temperature at atmospheric pressure would be set to about 125° C. At higher pressures, the temperature would be raised accordingly. When carrying out the Guerbet reaction at higher temperatures and pressures, adequate conversion rates may also be achieved with weaker bases, like KOH or NaOH.

The amount of the alkaline component in the reaction mixture is not critical. For sodium tert-butoxide rather similar Guerbet conversion rates were found in batch reactors at low temperature for amounts of the base ranging from 4 to 20 wt % of the primary alcohol starting mixture, whereby $Pd(Ac)_2$ has been used as catalyst in a concentration of 0.2 wt % with respect to the primary alcohol starting mixture. Lower catalyst concentrations have shown lower conversion rates. To achieve an adequate conversion rate with a proper base concentration throughout the process, a sodium tert-butoxide concentration of 8 wt % and a $Pd(Ac)_2$ concentration of 0.2 wt %, both with respect to the primary alcohol mixture to be converted, is used in some embodiments, whereby care is taken that any water evolving during the reaction process is removed from the mixture in order to avoid an inhibition of the reaction.

One or more primary alcohols of the formula $RCH_2CH_2OH$, where R is hydrogen or a straight or branched chain alkyl of 1 to 14 carbon atoms, are used as starting material for the Guerbet alcohol production. For example, multiple alcohols of different chain length and including secondary alcohols can be reacted. The use of alcohols with a carbon number of 4 or more, as for example 1-butanol, 1-pentanol and/or 1-hexanol, as starting material is preferred, whereby small amounts (as for example less than 10% by weight and particularly less than 5%) of 1-propanol may also be used advantageously in combination with one or more other starting alcohols.

The primary alcohol(s) may also contain secondary alcohols, ketones and aldehydes, since the latter would be intermediate reaction products when alcohols are the primary reactants. When aldehydes and ketones are added as reactants, a supplement of hydrogen is necessary to finally hydrogenate the reaction products to alcohols.

The Guerbet alcohols produced according to the above are a mixture of Guerbet alcohols, comprising a different number of carbon atoms in the chain and comprising at least a branching at the carbon atom adjacent to the carbon atom carrying the hydroxyl group.

The chain length of a Guerbet alcohol produced according to the Guerbet reaction as described above depends in principle on the primary alcohol(s) used as a starting material. When e.g. n-butanol is used as a starting material, 2-ethyl-1-hexanol is produced. A mixture of Guerbet alcohols is produced according to the different possible condensation reactions, using a mixture of starting alcohols differing from each other in the number of carbon atoms. When starting for example with 1-butanol ($C_4$) and 1-pentanol ($C_5$), the reaction results 2-ethyl-1-hexanol ($C_8$), 2-ethyl-1-heptanol ($C_9$), 2-propyl-1-hexanol ($C_9$), and 2-propyl-1-heptanol ($C_{10}$). With a feeding of a larger number of diverse alcohols, a greater variety of Guerbet alcohols is obtained. Furthermore, when starting with branched primary alcohols and/or reacting Guerbet alcohols already produced in the reaction mixture, multi-branched Guerbet alcohols are formed.

According to an advantageous embodiment, one or more of the Guerbet alcohols in the final mixture comprise two or more branches, particularly if it is the product of two or more subsequent condensation reactions. This further increases the variety of the Guerbet alcohols.

In the following tables, a non-exhaustive listing of examples is given for Guerbet alcohols obtained using one type or different types of primary alcohols as starting materials according to the following reaction scheme:

Alcohol 2→Aldehyde 2

Aldehyde 2+Alcohol 1→Guerbet alcohol

In the tables, the Guerbet alcohols are represented by the respective carbon number of the main chain and the kind and position of the substituent(s), the hydroxyl group of the alcohols being omitted in the table. The following abbreviations are used in the tables below: Me=methyl, diMe=dimethyl, triMe=trimethyl, Et=ethyl, Pr=propyl, iPr=—CH(CH$_3$)$_2$, Bu=butyl, iBu=—CH$_2$CH(CH$_3$)$_2$, sBu=—CH(CH$_3$)—CH$_2$CH$_3$, Pe=pentyl, A=amyl, iA=—CH$_2$CH$_2$CH(CH$_3$)$_2$, sA=—CH(CH$_3$)—CH$_2$CH$_2$CH$_3$, s'A=—CH$_2$—CH(CH$_3$)—CH$_2$CH$_3$, i=iso, s=sec, specifying the substituent's on the main chain of the Guerbet alcohol. The number preceding the substituent's gives the position of the substituent on the main chain. The number subsequent to "C" specifies the length of the main chain, i.e. stands for the number of carbon atoms in the main chain of the Guerbet alcohol with the hydroxyl group always in position 1 (primary alcohol). For example, 2MeC4 stands for 2-methylbutanol, 2Et4MeC5 stands for 2-ethyl-4-methyl-1-pentanol, and 2iBu4MeC5 stands for 2-isobutyl-4-methyl-1-pentanol. X stands for a reaction which is either impossible or difficult.

TABLE 2a

Guerbet reactions

| Alcohol 2 | Alcohol 1 | Methanol C1 | Ethanol C2 | Propanol C3 | Butanol C4 | Isobutanol iC4 |
|---|---|---|---|---|---|---|
| Methanol | C1 | x | Propanol | 2MeC3 | 2MeC4 | x |
| Ethanol | C2 | x | Butanol | 2MeC4 | 2EtC4 | x |
| Propanol | C3 | x | Pentanol | 2MeC5 | 2EtC5 | x |
| Butanol | C4 | x | C6 | 2MeC6 | 2EtC6 | x |
| Isobutanol | iC4 | x | 4MeC5 | 2,4diMeC5 | 2Et4MeC5 | x |
| Pentanol | C5 | x | C7 | 2MeC7 | 2EtC7 | x |
| 2MethylBuOH | 2MeC4 | x | 4MeC6 | 2,4diMeC6 | 2Et4MeC6 | x |
| 3MethylBuOH | 3MeC4 | x | 5MeC6 | 2,5diMeC6 | 2Et5MeC6 | x |

TABLE 2b

Guerbet reactions

| | Alcohol 1 | Pentanol | 2MethylBuOH | 3MethylBuOH |
|---|---|---|---|---|
| Alcohol2 | | C5 | 2MeC4 | 3MeC4 |
| Methanol | C1 | 2MeC5 | x | 2,3DiMeC4 |
| Ethanol | C2 | 2EtC5 | x | 2Et3MeC4 |
| Propanol | C3 | 2PrC5 | x | 2Pr3MeC4 |
| Butanol | C4 | 2PrC6 | x | 2iPrC6 |
| Isobutanol | iC4 | 2Pr4MeC5 | x | 2iPr4MeC5 |
| Pentanol | C5 | 2PrC7 | x | 2iPrC7 |
| 2MethylBuOH | 2MeC4 | 2Pr4MeC6 | x | 2iPr4MeC6 |
| 3MethylBuOH | 3MeC4 | 2Pr5MeC6 | x | 2iPr5MeC6 |

TABLE 2c

Guerbet reactions

| | | Hexanol | | | | | |
|---|---|---|---|---|---|---|---|
| Alcohol 2 | Alcohol 1 | C6 | 2MeC5 | 3MeC5 | 4MeC5 | 2,3DiMeC4 | 2EtC4 |
| Methanol | C1 | 2MeC6 | x | 2,3diMeC5 | 2,4diMeC5 | x | x |
| Ethanol | C2 | 2EtC6 | x | 2Et3MeC5 | 2Et4MeC5 | x | x |
| Propanol | C3 | 2PrC6 | x | 2Pr3MeC5 | 2Pr4MeC5 | x | x |
| Butanol | C4 | 2BuC6 | x | 2Bu3MeC5 | 2BuC6 | x | x |
| Isobutanol | iC4 | 2Bu4MeC5 | x | 2iBu3MeC5 | 2iBu4MeC5 | x | x |
| Pentanol | C5 | 2BuC7 | x | 2Pe3MeC5 | 2Pe4MeC5 | x | x |
| 2MethylBuOH | 2MeC4 | 2Bu4MeC6 | x | 2sBu4MeC6 | 2iBu4MeC6 | x | x |
| 3MethylBuOH | 3MeC4 | 2Bu5MeC6 | x | 2sBu5MeC6 | 2iBu5MeC6 | x | x |

TABLE 2d

| | | Guerbet reactions | | | | |
| | | | Heptanol | | | |
| Alcohol 2 | Alcohol 1 | C7 | 2MeC6 | 3MeC6 | 4MeC6 | 5MeC6 |
|---|---|---|---|---|---|---|
| Methanol | C1 | 2MeC7 | x | 2,3DiMeC6 | 2,4DiMeC6 | 2,5DiMeC6 |
| Ethanol | C2 | 2EtC7 | x | 2Et3MeC6 | 2Et4MeC6 | 2Et5MeC6 |
| Propanol | C3 | 2PrC7 | x | 2Pr3MeC6 | 2Pr4MeC6 | 2Pr5MeC6 |
| Butanol | C4 | 2BuC7 | x | 2Bu3MeC6 | 2Bu4MeC6 | 2Bu5MeC6 |
| Isobutanol | iC4 | 2iBuC7 | x | 2iBu3MeC6 | 2iBu4MeC6 | 2iBu5MeC6 |
| Pentanol | C5 | 2PeC7 | x | 2sAC7 | 2s'AC7 | 2iAC7 |
| 2MethylBuOH | 2MeC4 | 2Pe4MeC6 | x | 2sA4MeC6 | 2s'A4MeC6 | 2iA4MeC6 |
| 3MethylBuOH | 3MeC4 | 2Pe5MeC6 | x | 2sA5MeC6 | 2s'A5MeC6 | 2iA5MeC6 |

TABLE 2e

| | | Guerbet reactions | | | |
| | | | Heptanol | | |
| Alcohol2 | Alcohol 1 | 2,2diMeC5 | 2,3diMeC5 | 2,4diMeC5 | 3,3diMeC5 |
|---|---|---|---|---|---|
| Methanol | C1 | x | x | x | 2,3,3TriMeC5 |
| Ethanol | C2 | x | x | x | 2Et3,3diMeC5 |
| Propanol | C3 | x | x | x | 2Pr3,3diMeC5 |
| Butanol | C4 | x | x | x | 2Bu3,3diMeC5 |
| Isobutanol | iC4 | x | x | x | 2iBu3,3diMeC5 |
| Pentanol | C5 | x | x | x | 2Pe3,3diMeC5 |
| 2MethylBuOH | 2MeC4 | x | x | x | 2sA3,3diMeC5 |
| 3MethylBuOH | 3MeC4 | x | x | x | 2iA3,3diMeC5 |

TABLE 2f

| | | Guerbet reactions | | | |
| | | | Heptanol | | |
| Alcohol2 | Alcohol 1 | 3,4diMeC5 | 4,4diMeC5 | 2,2,3TriMeC4 | 2EtC5 |
|---|---|---|---|---|---|
| Methanol | C1 | 2,3,4TriMeC5 | 2,4,4TriMeC5 | x | x |
| Ethanol | C2 | 2Et3,4diMeC5 | 2Et4,4diMeC5 | x | x |
| Propanol | C3 | 2Pr3,4diMeC5 | 2Pr4,4diMeC5 | x | x |
| Butanol | C4 | 2Bu3,4diMeC5 | 2Bu4,4diMeC5 | x | x |
| Isobutanol | iC4 | 2iBu3,4diMeC5 | 2iBu4,4diMeC5 | x | x |
| Pentanol | C5 | 2Pe3,4diMeC5 | 2Pe4,4diMeC5 | x | x |
| 2MethylBuOH | 2MeC4 | 2sA3,4diMeC5 | 2sA4,4diMeC5 | x | x |
| 3MethylBuOH | 3MeC4 | 2iA3,4diMeC5 | 2iA4,4diMeC5 | x | x |

TABLE 2g

| | | Guerbet reactions | | | |
| | | | Heptanol | | |
| Alcohol2 | Alcohol 1 | 3EtC5 | 2Et2MeC4 | 2Et3MeC4 | Octanol C8 |
|---|---|---|---|---|---|
| Methanol | C1 | 2Me3EtC5 | x | x | 2MeC8 |
| Ethanol | C2 | 2Et3EtC5 | x | x | 2EtC7 |
| Propanol | C3 | 2Pr3EtC5 | x | x | 2PrC8 |
| Butanol | C4 | 2Bu3EtC5 | x | x | 2BuC8 |
| Isobutanol | iC4 | 2iBu3EtC5 | x | x | 2iBuC8 |
| Pentanol | C5 | 2Pe3EtC5 | x | x | 2PeC8 |
| 2MethylBuOH | 2MeC4 | 2sA3EtC5 | x | x | 2sAC8 |
| 3MethylBuOH | 3MeC4 | 2iA3EtC5 | x | x | 2s'AC8 |

Figure 2:
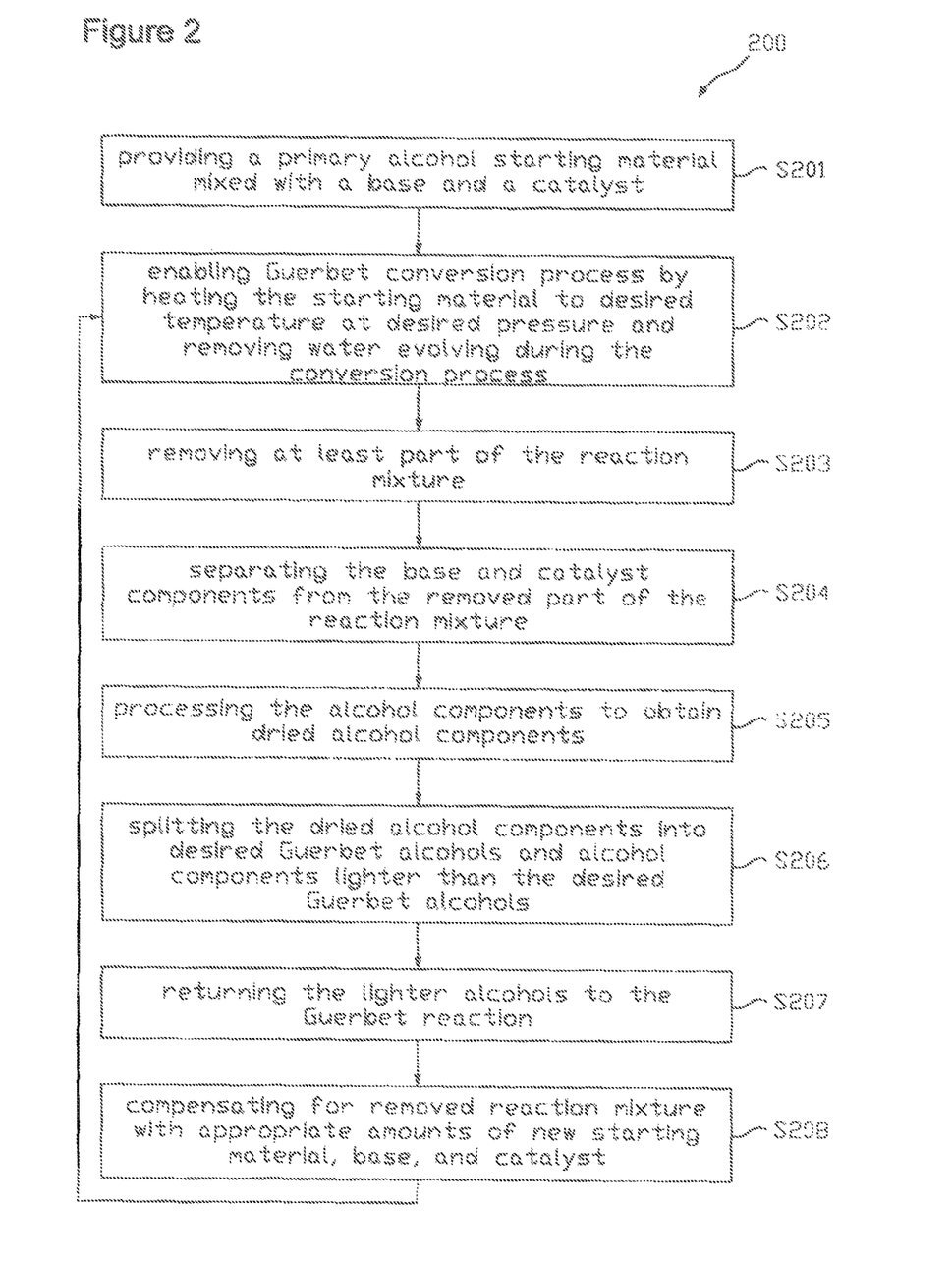
FIG. 2 shows a flow chart illustrating the basic steps of a method for synthesising Guerbet alcohols from a starting material comprising one or more primary alcohols with a system according to FIG. 1.

The flow chart of FIG. 2 illustrates the basic steps of a method 200 for synthesising a mixture of Guerbet alcohols from a one or more primary alcohols as described above. The method starts in step S201 with the provision of one or more primary alcohols (e.g. a blend corresponding to the feedstock mentioned above) mixed with a base (e.g. sodium tert-butoxide) and a catalyst (e.g. a heterogeneous catalyst like Ni/MgO/SiO$_2$ or a homogeneous catalyst like palladium (II)-acetate). The Guerbet conversion is enabled in step S202 by heating the mixture to a desired process temperature at the desired pressure (e.g. 125° C. at about 1 bar or 200° C. at about 9 bar) with the water evolving during the process being removed on a permanent basis. Either after a predetermined time or depending on the water content of the vapour transferred to the water separation unit 20—when the process is preferably operated in a continuous mode the contact time in the reaction section is constant and determined by the reactant flow—, part of the reaction mixture will be removed from the reactor 10 in step S203, with the mixture's alcohol components being separated from the base and catalyst components in the first after-treatment system in step S203 and transferred to the second after-treatment in step S204. In the second after-treatment system, the alcohol components are further processed in step 205 for obtaining dried alcohol components with the dried alcohols then being split into those desired and those lighter than the desired ones in step 206. The latter are in step S207 then returned to the Guerbet reaction taking place within reactor 10. The method may further comprise an optional step 208 compensating for the removed reaction mixture with appropriate amounts of new feedstock, base and catalyst, which may be performed simultaneously to one or more of the steps 203 to 207, or like these on a continuous basis, when a continuous process of manufacture is desired.

The present invention enables a large scale production of multi-branched Guerbet alcohols where the final distribution of Guerbet alcohols can be controlled by splitting the desired reaction products from the lighter ones and returning the latter into the reaction chamber for further reaction processing. Respective Guerbet alcohols may be used as additives for fuels like diesel or jet fuels, where they increase the electric conductivity and thus decrease the probability of ignition by static electricity. The Guerbet alcohols may further be used as precursors of esters such as acrylates, methacrylates, phthalates or the like. The Guerbet alcohols may further also be hydrodeoxygenated and possibly further refined for obtaining gasoline, diesel fuel or aviation gasoline and jet fuel constituents. The Guerbet alcohols may also be dehydrated to alpha-olefins, which can then be polymerized or oligomerized. The Guerbet alcohols may also be used for producing surfactants that are e.g. suited for utilisation in petroleum industry operations.

The present invention includes the following numbered aspects, embodiments, and features, in any order and/or in any combination:

1. A method for preparing a mixture of Guerbet alcohols, the method comprising:
providing a starting material comprising one or more primary alcohols of the formula RCH$_2$CH$_2$OH, where R is hydrogen or a straight or branched chain alkyl of 1 to 14 carbon atoms;
providing a base;
providing a catalyst;
mixing the starting material with the base and the catalyst and heating the thus obtained reaction mixture to a process temperature above the boiling point of water under reaction conditions while removing the water resulting from the thus obtained condensation and dehydration of the primary alcohols;
removing at least part of the reaction mixture;
separating the desired Guerbet alcohols from the removed part of the reaction mixture; and
returning the other alcohols and optionally other intermediates from the removed part of the reaction mixture to the reaction mixture.

2. The method of any preceding or following embodiment/feature/aspect, wherein the starting material further contains primary alcohols in which the carbon atom in beta-position is bonded to two or three alkyl groups, secondary alcohols, ketones and aldehydes, and hydrogen is added to the reaction mixture or the removed part of the reaction mixture.

3. The method according to of any preceding or following embodiment/feature/aspect, wherein the starting material contains at least two primary alcohols selected from the group comprising n-propanol, n-butanol, n-pentanol, n-hexanol.

4. The method to of any preceding or following embodiment/feature/aspect, wherein the base is selected from the group consisting of sodium tert-butoxide, potassium hydroxide, sodium hydroxide, and heterogeneous bases, which may optionally be doped.

5. The method according to of any preceding or following embodiment/feature/aspect, wherein the catalyst is a homogenous catalyst or a heterogeneous catalyst selected from the group consisting of Pd(OAc)$_2$, Pd/C, Pt/C, Cu—Zn—O, Cu—Cr—O, hydrotalcites and hydroxylapatites doped with metals, Raney Ni, and Ni—MgO/SiO$_2$ 6. The method according to of any preceding or following embodiment/feature/aspect, wherein the catalyst is a solid heterogeneous catalyst provided in a fixed bed, or a slurry fluidized bed, or a mobile bed.

7. The method according to of any preceding or following embodiment/feature/aspect, wherein the alcohols returned to the reaction mixture have a lower boiling point than the desired Guerbet alcohols.

8. The method according to of any preceding or following embodiment/feature/aspect, wherein the process temperature corresponds to the boiling point of the starting material under reaction conditions.

9. The method according to of any preceding or following embodiment/feature/aspect, wherein the reaction process is performed at a pressure in the range of 1 to 20 bar.

10. The method according to of any preceding or following embodiment/feature/aspect, wherein the starting material is pre-treated with respect to removing acidic components, ester components, water, or a combination thereof, prior to being fed to mixing.

11. A system for synthesising Guerbet alcohols from a starting material according to the method of any preceding or following embodiment/feature/aspect, wherein the system comprising:
a reactor adapted for receiving the starting material, a base, and a catalyst to form a reaction mixture, and for heating the reaction mixture to a temperature above the boiling point of water under reaction conditions to obtain a Guerbet condensation and dehydration process;
a water separation unit connected to the reactor and adapted to receive from the reactor vapor evolving in the progress of the Guerbet condensation process, and to remove water from the vapor; and
an after-treatment system connected to the reactor and adapted to receive from the reactor at least part of the reaction mixture, separating the desired Guerbet alcohols from the removed part of the reaction mixture, and returning the other alcohols and optionally other intermediates from the removed part of the reaction mixture to the reactor.

12. The system according to of any preceding or following embodiment/feature/aspect, wherein the reactor is one of a stirred tank reactor, a fixed bed reactor, a mobile bed reactor, and a fluidized bed reactor.

13. The system according to of any preceding or following embodiment/feature/aspect, wherein the after-treatment system comprises a first after-treatment system adapted to separate a catalytic component and an alkaline component from the part of the reaction mixture received from the reactor, and a second after-treatment system connected to the first after-treatment system and adapted to separate the desired Guerbet alcohols from the part of the reaction mixture treated by the first after-treatment system and to return the other alcohols from the part of the reaction mixture treated by the first after-treatment system, to the reactor.

14. The system according to of any preceding or following embodiment/feature/aspect, wherein wherein the second after-treatment system comprises a liquid-liquid mixer-settler configuration adapted to receive the reaction mixture treated by the first after-treatment system and to provide a phase separation of the components present in the mixture, an alcohols column adapted to receive the primarily alcohol components containing phase from the liquid-liquid mixer-settler configuration and to dry the alcohol components, and an alcohols splitter column connected to the alcohols column and the reactor, and being adapted to separate the desired Guerbet alcohols from the dried alcohol components and to return the remaining dried alcohols to the reactor.

15. The system according to of any preceding or following embodiment/feature/aspect, wherein the second after-treatment system further comprises a water column adapted to receive the primarily water containing phase from the liquid-liquid mixer-settler configuration, separate water from the primarily water containing phase, and return alcohols containing water to the liquid-liquid mixer-settler configuration.

16. The system according to of any preceding or following embodiment/feature/aspect, wherein the water separation unit is further adapted to return the vapor components different than the separated water, to the reactor, and to provide the still alcohols containing separated water to the liquid-liquid mixer-settler configuration.

17. The system according to of any preceding or following embodiment/feature/aspect, further comprising a pre-treatment facility adapted to remove acidic components, ester components, water, or a combination thereof, from the starting material prior to supplying the starting material to the reactor.

18. The method of of any preceding or following embodiment/feature/aspect, further comprising adding the mixture of Guerbet alcohols to a gasoline, diesel fuel, aviation gasoline, jet fuel, or a combination thereof.

19. The method of of any preceding or following embodiment/feature/aspect, further comprising processing the mixture of Guerbet alcohols optionally with other components to form a surfactant, an alpha-olefin, an alpha-olefin polymer, an alpha-olefin oligomer, or a combination thereof.

EXAMPLES

The below examples have been obtained by simulations based on the system illustrated in the piping and instrumentation diagram shown in FIG. 1. The simulations have been carried out using the Aspen Plus® chemical modelling system from Aspen Technology Inc., USA. The simulation results are summarised in the tables below, listing the process parameters together with the mass flow of several reactants, intermediate products, and products at different positions of the system illustrated in FIG. 1. The positions, which are referred to as checkpoints in the tables, are indicated in FIG. 1 by "measurement point" symbols a to h.

Example 1

In this example, the simulation has the reactor operated at substantially atmospheric pressure and at a temperature of about 125° C. As starting material, a blend of primary alcohols is used, containing 2.9 wt % 1-propanol, 57.8 wt % 1-butanol, 23.7 wt % 1-pentanol, and 15.3 wt % 1-hexanol. The starting material is provided at an elevated pressure for facilitating the feeding of the reactor. Since the low temperature results in slow reaction kinetics, a stronger base was required; therefore sodium tert-butoxide has been used. The results for the simulation are shown below in the Table SL1.

TABLE SL1

| | a | b | c | d | e | f | g | h |
|---|---|---|---|---|---|---|---|---|
| Checkpoint | | | | | | | | |
| Temperature in ° C. | 125 | 125 | 125 | 50 | 47 | 99 | 111 | 176 |
| Pressure in bar | 3 | 1.01 | 1.01 | 1.01 | 0.4 | 1.01 | 1.01 | 1.01 |
| Mole Flow in kmol/h | 137.6 | 312.4 | 160.3 | 160.3 | 67.7 | 189.2 | 110.7 | 78.6 |
| Mass Flow in kg/h | 11002 | 20773 | 15784 | 15784 | 1348 | 17981 | 8092 | 9889 |
| Mass Flow in kg/h | | | | | | | | |
| C2 alcohol | 0.2 | 0.5 | 0.1 | 0.1 | 0.4 | 0.2 | 0.2 | 0 |
| C3 alcohol | 317 | 1891 | 382 | 382 | 41 | 1270 | 1269 | 1 |
| C4 alcohol | 6364 | 12343 | 4124 | 4124 | 101 | 5358 | 5331 | 27 |
| C5 alcohol | 2607 | 3582 | 2019 | 2019 | 2 | 2193 | 1274 | 919 |
| C6 alcohol | 1682 | 614 | 1047 | 1047 | 3 | 1047 | 52 | 995 |
| C7 alcohol | 0 | 76 | 250 | 250 | 0 | 250 | 1 | 250 |
| C8 alcohol | 0 | 646 | 4469 | 4469 | 1 | 4469 | 0 | 4469 |
| C9 alcohol | 0 | 113 | 1764 | 1764 | 0 | 1764 | 0 | 1764 |
| C10 alcohol | 0 | 59 | 1457 | 1457 | 0 | 1457 | 0 | 1457 |
| Water | 0 | 983 | 84 | 84 | 1176 | 9 | 9 | 0 |
| 2-Buten-1-ol | 32.2 | 464.8 | 187.4 | 187.4 | 23.7 | 165 | 156.2 | 8.8 |

As can be seen from Table SL1, the reaction can be operated with recycling of the unconverted light compounds. The mass yield of the reaction reaches 90% looking at mass flow rate of product released in h versus mass flow rate of reactants in a. The product distribution contains a low amount of C4 alcohols but some C5 alcohols. The process could have been adjusted to recycle more C5 alcohols to the reactor and so the product would contain less C5 alcohols.

Example 2

In this example, the simulation has the reactor operated at a pressure of substantially 9.0 bar abs. enabling an operation at a temperature of about 200° C. without excessive evaporation of the components present in the reaction medium. As starting material, again a blend of primary alcohols is used, containing 2.9 wt % 1-propanol, 57.8 wt % 1-butanol, 23.7 wt % 1-pentanol, and 15.3 wt % 1-hexanol. The starting material is provided at an elevated pressure for facilitating a feeding of the reactor. Since the higher temperature results in faster reaction kinetics, it was possible to use a weak base like NaOH or KOH. The results for the simulation are shown below in the Table SL2.

TABLE SL2

| | a | b | c | e | f | g | h |
|---|---|---|---|---|---|---|---|
| Checkpoint | | | | | | | |
| Temperature in ° C. | 189 | 203 | 203 | 47 | 99 | 112 | 176 |
| Pressure in bar | 10 | 9 | 9 | 0.4 | 1.01 | 1.01 | 1.01 |
| Mole Flow in kmol/h | 137.6 | 349.4 | 179.3 | 68 | 202.7 | 124.1 | 78.6 |
| Mass Flow in kg/h | 11002 | 24280 | 16802 | 1357 | 19082 | 9196 | 9886 |
| Mass Flow in kg/h | | | | | | | |
| C2 alcohol | 0.2 | 0.3 | 0.3 | 0.5 | 0.3 | 0.3 | 0 |
| C3 alcohol | 317 | 2113 | 570 | 29 | 972 | 971 | 0 |
| C4 alcohol | 6364 | 13844 | 5151 | 118 | 6534 | 6502 | 33 |
| C5 alcohol | 2607 | 4805 | 1741 | 2 | 2428 | 1509 | 919 |
| C6 alcohol | 1682 | 752 | 1046 | 2 | 1045 | 52 | 993 |
| C7 alcohol | 0 | 94 | 238 | 0 | 238 | 0 | 238 |
| C8 alcohol | 0 | 1111 | 4481 | 1 | 4480 | 0 | 4480 |
| C9 alcohol | 0 | 205 | 1754 | 0 | 1754 | 0 | 1754 |
| C10 alcohol | 0 | 119 | 1460 | 0 | 1460 | 0 | 1460 |
| Water | 0 | 886 | 179 | 1181 | 10 | 10 | 0 |
| 2-Buten-1-ol | 32.2 | 350.8 | 182.3 | 23 | 160.4 | 150.9 | 9.5 |

As can be seen from a comparison with Table SL1, in this configuration the reaction temperatures are higher but the downstream processing is done at the same temperature. This allows to have faster reactions and to reduce the size of the reactors accordingly, generating a capital cost advantage. In addition in this configuration, the mass yield is still around 90% and the product distribution remains unaffected. The overall process designed with its recycles and features allow to operate with a high yield.

Example 3

In this example, the simulation has been carried out on a system modified with respect to that shown in FIG. 1. The modifications are designed to enable a system performing the Guerbet conversion with a starting material composed of a blend of primary alcohols as used in above examples 1 and 2 and a supplement of aldehydes. The addition of aldehydes is reflected in the simulation by an extra reaction butanol butyraldehyde. The modifications concern an added feed of ethylene for hydrogen capture to the reactor, a separator between the reactor 10 and the water column for removing the ethane from the vapour supplied to the water column 20, a post treatment unit (located with respect to FIG. 1 between the first after-treatment system 30 and checkpoint d) for hydrogenating the output from the first after-treatment system 30, and separators downstream of the alcohols column 43 and the alcohols splitter column 44 for removing by-products from the respective streams. The results for the simulation are shown below in the Table SL3.

TABLE SL3

| | a | b | d | e | g | h |
|---|---|---|---|---|---|---|
| Checkpoint | | | | | | |
| Temperature in ° C. | 125 | 125 | 125 | 52.3 | 111.5 | 174.9 |
| Pressure in bar | 3 | 1.013 | 1.013 | 0.4 | 1.013 | 1.013 |
| Mole Flow in kmol/h | 137.6 | 324.0 | 164.1 | 64.8 | 115.0 | 78.7 |
| Mass Flow in kg/h | 11002 | 21624 | 16056 | 1262 | 8398 | 9884 |
| Mass Flow in kg/h | | | | | | |
| C2 alcohol | | 0.15 | 0.34 | 0.05 | 0.34 | 0.12 | 0 |
| C3 alcohol | 316.9 | 1824.9 | 345.7 | 32.9 | 1252.3 | 0.278 |
| C4 alcohol | 6363.8 | 12308.3 | 4119.5 | 77.7 | 5315.5 | 26.7 |
| C5 alcohol | 2607.1 | 3426.3 | 1999.4 | 2.1 | 1225.8 | 941.9 |
| C6 alcohol | 1681.9 | 632.4 | 1051.1 | 2.0 | 52.6 | 998.5 |
| C7 alcohol | 0 | 78.0 | 250.11 | 0.06 | 0.52 | 249.5 |
| C8 alcohol | 0 | 674.7 | 4452.4 | 0.46 | 0.18 | 4451.2 |
| C9 alcohol | 0 | 121.91 | 1755.4 | 0.02 | 0.001 | 1754.9 |

TABLE SL3-continued

| | a | b | d | e | g | h |
|---|---|---|---|---|---|---|
| C10 alcohol | 0 | 6é; à | 1441.6 | 0.07 | 0 | 1441.2 |
| C2H6 | 0 | 2.57 | 0.004 | 3.994 | 0 | 0 |
| H2O | 0 | 981.3 | 80.6 | 1133.4 | 9.14 | 0 |
| ethylene | 0 | 0 | 0 | 0 | 0 | 0 |
| butanal | 0 | 2.90 | 0 | 4.02 | 0.11 | 0 |
| buten-1-ol | 32.15 | 1506.4 | 558.4 | 5.89 | 541.6 | 18.6 |
| 2-ethyl hexenal | 0 | 1.96 | 0.87 | 0.001 | 0.07 | 0.80 |
| 2-Ethyl hexanal | 0 | 0.17 | 1.06 | 0.001 | 0.18 | 0.88 |

In this example, a reactor (additional finishing hydrogenation reactor) is included between points c and d. The conversion of butanal to butanol, 2-ethylhexenal to 2-ethylhexanal, and of the latter to 2-ethylhexanol have been assumed with partial conversion in some cases. Results show that the process can still be effective if aldehydes are present in the feedstock, injected for example within the loop or formed by the reaction. Aldehydes do not accumulate and are either reacted in the reactor or hydrogenated to alcohols. In this simulation light aldehydes, which are also fast reacting reaction intermediates, such as n-butanal present in stream g, are converted in reactor 10, where they have been fed, injected or formed. If not converted, these lighter aldehydes would tend to accumulate in the loop between liquid-liquid mixer-settler (or decanter) 41 and alcohols column 43. This could be prevented by partly or fully returning them back to the reactor upon their removal from the loop by separation or purging. Heavier aldehydes such as 2-ethyl hexenal and 2-ethyl hexanal would tend to leave the reactor by outlet 12. So in absence of a hydrogenation finishing reactor most of them leave the process by product stream h, thus contaminating it. When their concentration exceeds the tolerances, a finishing reactor has to be deployed to convert them into alcohols by a hydrogenation between point c and point d under sufficiently stringent conditions.

It is apparent that variations and modifications to the present teachings are possible without departing from its scope and spirit. It is therefore to be understood that the appended claims are to be construed as encompassing all features of patentable novelty that reside in the present teachings, including all features that would be treated as equivalent thereof by those skilled in the art to which the present teachings pertain. All US, International, and foreign patents and publications, as well as non-patent literature, referred to herein are hereby incorporated herein by reference in their entireties. All publications, patents, and patent applications mentioned in this specification are herein incorporated by reference to the same extent as if each individual publication, patent, or patent application was specifically and individually indicated to be incorporated by reference.

While embodiments of the present teachings have been shown and described herein, it will be apparent to those skilled in the art that such embodiments are provided by way of example only. Numerous variations, changes, and substitutions will now occur to those skilled in the art without departing from the present teachings. It is to be understood that various alternatives to the embodiments of the disclosure described herein may be employed in practicing the present teachings. It is intended that the following claims define the scope of the present teachings and that methods and structures within the scope of these claims and their equivalents be covered thereby.

LIST OF REFERENCE SIGNS 100 process engineering system for a synthesis of Guerbet alcohols from a mixture of primary alcohols
10 reactor
11 feed port
12 discharge port
13 vapour outlet
14 reflux inlet
15 base inlet port
16 catalyst inlet port
20 water separation unit
21 vapour inlet port
22 alcohol outlet port
23 water outlet port
30 first after-treatment system
40 second after-treatment system
41 liquid-liquid mixer-settler configuration
42 water column
43 alcohols column
44 separation system/alcohols splitter column
50 pretreatment facility
200 simplified method for synthesising Guerbet alcohols from a mixture of primary alcohols
S201-S208 basic process steps

The invention claimed is:

1. A method for preparing a mixture of Guerbet alcohols, the method comprising:
providing a starting material comprising a blend of at least two different primary alcohols, each of the at least two different primary alcohols independently being of the formula RCH$_2$CH$_2$OH, where R is hydrogen or a straight or branched chain alkyl group of 1 to 14 carbon atoms;
providing a base;
providing a catalyst;
mixing the starting material with the base and the catalyst in a reactor to form a reaction mixture;
heating the reaction mixture to a process temperature above the boiling point of water and under reaction conditions to cause condensation and dehydration of the at least two primary alcohols of the blend and to evolve vapor including water vapor;
removing the evolved vapor including water vapor from the reactor and feeding the removed vapor to a water separation unit, the water separation unit comprising a water outlet port;
removing part of the reaction mixture from the reactor, to form a removed part, and feeding the removed part to a liquid-liquid mixer-settler, the removed part comprising a mixture of Guerbet alcohols having respective boiling points, and alcohols having lower boiling points than the boiling points of the Guerbet alcohols;
feeding water from the water outlet port of the water separation unit, into the liquid-liquid mixer-settler to form a settler mixture;
separating an organic fraction from an aqueous fraction in the liquid-liquid mixer-settler;

feeding the organic fraction into an alcohols column;

forming dried alcohols from the organic fraction in the alcohols column;

separating the dried alcohols into a mixture of Guerbet alcohol products and the alcohols having lower boiling points than the boiling points of the Guerbet alcohols;

returning the alcohols having lower boiling points than the boiling points of the Guerbet alcohols, to the reaction mixture in the reactor; and compensating for the removed part of the reaction mixture by adding appropriate amounts of new starting material comprising a blend of at least two different primary alcohols, base, and catalyst, to the reaction mixture in the reactor, for balancing the respective losses.

2. The method according to claim 1, wherein the starting material further contains primary alcohols in which a carbon atom in a beta-position is bonded to two or three alkyl groups, secondary alcohols, ketones, and aldehydes, and the method further comprises adding hydrogen gas ($H_2$) to the reaction mixture or the removed part of the reaction mixture.

3. The method according to claim 1, wherein the blend of at least two different primary alcohols contains at least two primary alcohols selected from n-propanol, n-butanol, n-pentanol, and n-hexanol.

4. The method according to claim 1, wherein the base is selected from the group consisting of sodium tert-butoxide, potassium hydroxide, sodium hydroxide, and heterogeneous bases, which may optionally be doped.

5. The method according to claim 1, wherein the catalyst is a homogenous catalyst or a heterogeneous catalyst selected from the group consisting of Pd(OAc)$_2$, Pd/C, Pt/C, Cu—Zn—O, Cu—Cr—O, hydrotalcites and hydroxylapatites doped with metals, Raney Ni, and Ni—MgO/SiO$_2$.

6. The method according to claim 5, wherein the catalyst is a solid heterogeneous catalyst provided in a fixed bed, or a slurry fluidized bed, or a mobile bed.

7. The method according to claim 1, wherein the process temperature corresponds to a boiling point of the starting material under reaction conditions.

8. The method according to claim 1, wherein the reaction conditions comprise a pressure in the range of from 1 to 20 bar.

9. The method according to claim 1, wherein the starting material is pretreated by a process comprising one or more of ion exchange, neutralization, and dehydration, to remove acidic components, ester components, water, or a combination thereof, before mixing the starting material with the base and the catalyst in the reactor.

10. The method of claim 1, further comprising adding the mixture of Guerbet alcohols to a gasoline, diesel fuel, aviation gasoline, jet fuel, or a combination thereof.

11. The method of claim 1, further comprising processing the mixture of Guerbet alcohols optionally with other components to form a surfactant, an alpha-olefin, an alpha-olefin polymer, an alpha-olefin oligomer, or a combination thereof.

12. The method of claim 1, wherein the step of compensating is performed simultaneously with the step of returning.

13. The method of claim 1, wherein the step of compensating is performed after the step of returning.

* * * * *